United States Patent [19]

Sanderson et al.

[11] Patent Number: 5,025,112
[45] Date of Patent: Jun. 18, 1991

[54] PURIFICATION OF CUMENE RECYCLE STREAMS

[75] Inventors: John R. Sanderson, Leander; Edward T. Marquis; John F. Knifton, both of Austin, all of Tex.

[73] Assignee: Texaco Chemical Company, White Plains, N.Y.

[21] Appl. No.: 580,035

[22] Filed: Sep. 10, 1990

[51] Int. Cl.$^5$ .......................... C07C 7/00; C07C 7/17
[52] U.S. Cl. .................................. 585/852; 585/800; 585/823; 585/833; 585/858
[58] Field of Search ............... 585/800, 823, 833, 852, 585/858

[56] References Cited
U.S. PATENT DOCUMENTS 3,803,255  4/1974  Ellis et al. .......................... 585/823

Primary Examiner—Curtis R. Davis
Assistant Examiner—Nhat Phan
Attorney, Agent, or Firm—Jack H. Park; Kenneth R. Priem; Cynthia L. Kendrick

[57] ABSTRACT

A method for purifying a cumene recycle stream by removing 2-phenyl-2-propanol and cumene hydroperoxide before the cumene is distilled and recycled to the peroxidation reactor which comprises reacting the recycle cumene in the presence of an acid treated montmorillonite clay of the formula:

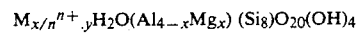

$$M_{x/n}{}^{n+} \cdot yH_2O(Al_{4-x}Mg_x)(Si_8)O_{20}(OH)_4$$

or in the presence of a catalyst comprising phosphoric acid on silica.

6 Claims, No Drawings

PURIFICATION OF CUMENE RECYCLE STREAMS

BACKGROUND OF THE INVENTION

1. Field of the Invention

This invention relates to an improved method for purification of a cumene recycle stream and more particularly this invention relates to methods for removing cumene hydroperoxide and 2-phenyl-2-propanol impurities from a cumene recycle stream in order to reduce the loss in selectivity to cumene hydroperoxide resulting from peroxidation of recycle cumene containing impurities. The impurities can be removed by treatment with a clay catalyst in one embodiment and, in another embodiment are removed by a catalyst comprising phosphoric acid on silica.

2. Description of Related Art

The cumene process is used to manufacture more than 90% of the phenol produced today. In the process, propylene is reacted with benzene to produce cumene.

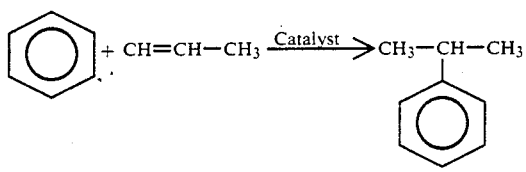

After purification, the cumene is reacted with either air or oxygen to produce cumene hydroperoxide.

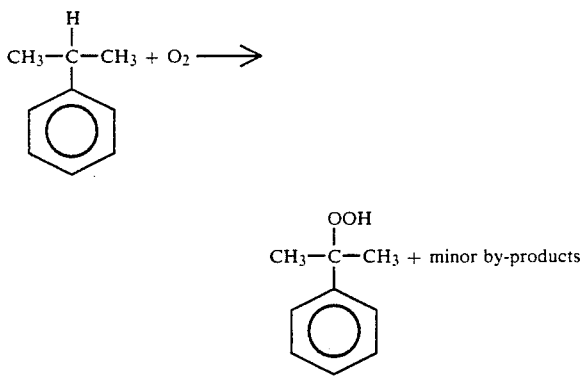

Careful adjustment of reaction conditions is necessary to obtain good reaction rates without loss of yield. In most industrial processes, the conversion of cumene to products is held to 20–40%. Under the best conditions yields of over 90% to cumene hydroperoxide may be obtained.

Most of the unconverted cumene is removed from the oxidation product by vacuum distillation and recycled to the oxidation reactor. The concentration of cumene hydroperoxide is then 75–85%.

The next stage in the process is the cleavage of the peroxide to phenol and acetone which can be represented as follows:

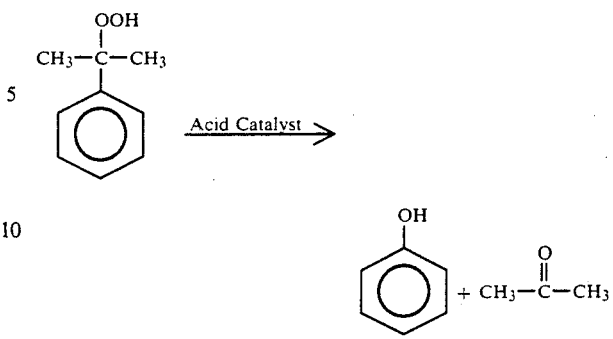

The product from the cleavage stage contains phenol, acetone, cumene, acetophenone, 2-phenyl-2-propanol and other minor byproducts. Phenol and acetone are separated by distillation.

The cumene present in the cleavage step is distilled but still contains impurities. It is combined with the cumene isolated from the concentration step. This combined product is recycled to the oxidation reactor, but contains various impurities such as cumene hydroperoxide, 2-phenyl-2-propanol, acetophenone, α-methyl styrene and phenol. α-Methyl styrene and phenol are especially detrimental in the oxidation. These two impurities are difficult to remove by distillation since 2-phenyl-2-propanol decomposes to give α-methyl styrene and cumene hydroperoxide may decompose to give phenol and acetone during distillation.

There is an overview of the technology and economics relating to the production of phenol in Chem. Systems Report No. 79-2, September, 1979, p. 155. It is noted that an important factor influencing the oxidation rate is the purity of the cumene feed, since small amounts of inhibitors, such as sulfur compounds, phenols, aniline or styrenes present in the feed may break the reaction chain by tying up free radicals. Other compounds that catalyze the decomposition of the hydroperoxide are soluble compounds of copper, cobalt and manganese. Acceptable oxidation and conversion rates can be achieved with normal industrial cumene without extensive feed pretreatment, but this generally leads to lower conversion efficiencies and increased side reactions. In the market recently the requirements for improved conversion efficiencies have resulted in the tightening of cumene feed specifications. Purities as high as 99.9 weight percent are now commonly required for the production of chlorination-grade phenol. An alkali wash cumene feed pretreatment is also generally beneficial.

In *Kirk-Othmer Encyclopedia of Chemical Technology*, 7, 373(1982) there is a discussion of various methods for producing phenol and of the economic aspects related thereto. At page 380, second paragraph it is noted that the USP specification for phenol requires a phenol content of not less than 98%.

The following early patents provide background for the oxidation of aromatic hydrocarbons:
U.S. Pat. No. 2,447,400
U.S. Pat. No. 2,547,400
U.S. Pat. No. 2,632,772
U.S. Pat. No. 2,632,773
to produce products such as acetophenone, peroxides of alkylbenzenes, etc.

U.S. Pat. No. 2,706,708 discloses a process for separating cumene from cumene hydroperoxide, wherein the hydroperoxide is made substantially free of dialkylarylmethane by stripping the dialkylarylmethane from dialkylaryl methyl hydroperoxide and passing it through a separation zone.

An improvement in a method for producing cumene hydroperoxide is disclosed in U.S. Pat. No. 3,049,477. The improvement comprises fractional distillation of the oxidation reaction mixture in a still to obtain an overhead fraction comprising cumene, water and organic acids and a bottoms product comprising cumene hydroperoxide which occurs in a concentration higher than it occurred in the oxidation mixture, the improvement comprising recycling the total overhead fraction and recycling at least the cumene to the oxidation step and adding to the still as a liquid reflux a fresh cumene characterized by being substantially dry and having a pH not less than 5.

U.S. Pat. No. 3,092,587 demonstrates the use of thin film and reflux measures to produce high percentage solutions of organic peroxides from low percentage solutions of alkylated aromatic hydrocarbon organic peroxides.

It was disclosed in U.S. Pat. No. 3,141,046 that an effective catalyst for the oxidation of cumene to hydroperoxide is an alkali salt of a carboxylic acid of the general formula:

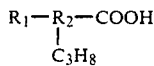

where $R_1$ represents an alkyl or aryl group and $R_2$ represents a straight or branched-chain trivalent saturated aliphatic hydrocarbon group. The invention disclosed in this patent comprises oxidizing cumene by treatment at an elevated temperature with molecular oxygen in the presence of the above-described alkali metal salt of a carboxylic acid.

U.S. No. 3,290,384 discloses a method for the oxidation of aralkyl hydrocarbons such as isopropyl benzene to aralkyl hydroperoxides in the presence of a specific class of heavy metal catalysts.

In U.S. No. 3,519,690 there is disclosed a process for the separation of aliphatic or aromatic organic hydroperoxides from their liquid mixtures by thermal diffusion.

In the invention of U.S. No. 3,647,886 certain hydrocarbyl hydroperoxides are formed by contacting a hydrocarbyl hydrocarbon with an oxygen-containing gas in the presence of KF.

There is disclosed in U.S. No. 3,833,663 a process for the oxidation of cumene to cumene hydroperoxide in which cumene is contacted in the liquid phase in the presence of cumene hydroperoxide at a temperature in the range of 40° to 140° C. with a gas containing free oxygen over a catalyst comprising a fluoride of an alkali or alkaline earth metal.

In *Liquid Phase Oxidation of Hydrocarbons,* Emanual, N. M., et al., Plenum Press (1967), Chapter IX, titled "The Oxidation of Individual Hydrocarbons", it is noted at page 314 that benzoic acid accelerates the decomposition of the hydroperoxide into radicals. Apparently the addition of certain acids inhibits the oxidation of cumene, causing decomposition of the peroxide into phenol and acetone. As little as 0.02% by weight of formic acid almost completely inhibits the oxidation of cumene, Ibid., p. 315.

It was found the pH of the medium had an additional influence on the kinetics of the oxidation of cumene. For example, alkali-containing compounds were found to have an accelerating action. In addition, the inhibiting action of phenol on the oxidation is greatly weakened in the presence of alkali, Ibid.

Emanual, et al. provided evidence to indicate that in the presence of an alkali, decomposition takes place by the overall equation:

It was concluded that the accelerating effect of alkali is connected, not only with the neutralization of acidic products, but also with an increase in the rate of initiation of the chains.

In a strongly alkaline medium (5–10% NaOH) the oxidation of cumene does not go selectively, although the rate is high and the yield of hydroperoxide does not exceed 50% of the oxygen absorbed. Acids formed in the oxidation of cumene at 85° C. in an aqueous emulsion lower the pH of the emulsion and retard the reaction. At a pH of about 4–7 (neutral or acidic) oxidation takes place slowly, similar to homogeneous oxidation at this temperature.

It would be a substantial advance in the art in this field if an efficient method were available which would provide a way to remove 2-phenyl-2-propanol and cumene hydroperoxide from the cumene recycle stream so that subsequent distillation would allow production of the recycle cumene essentially free of detrimental impurities.

SUMMARY OF THE INVENTION

In accordance with the forgoing the novel method of this invention provides for removing impurities including 2-phenyl-2-propanol and cumene hydroperoxide from a cumene recycle stream by passing the cumene over a catalyst from the group consisting of an acidic clay catalyst or a phosphoric acid on silica catalyst. The method is very advantageous in that it provides a means for decomposition of cumene hydroperoxide and other impurities before the distillation stage, thus providing greater purity in the cumene for recycling.

DESCRIPTION OF THE PREFERRED EMBODIMENT

In the method of this invention the cumene hydroperoxide and 2-phenyl-2-propanol are effectively removed from the cumene recycle stream by reacting the cumene over a catalyst from the group consisting of:

1. An acidic clay catalyst
2. A phosphoric acid on silica catalyst to provide a recycled cumene of much greater purity which upon distillation allows for a substantially greater selectivity to the desired cumene hydroperoxide.

The feedstock comprises unconverted cumene remaining after peroxidation of cumene to cumene hydroperoxide. This recycle cumene contains impurities such as cumene hydroperoxide and 2-phenyl-2-propanol which, if present, can decompose during distillation, producing acetone, phenol, water and α-methyl styrene. Cumene containing these impurities cannot be effectively purified by distillation; the impurities result in a 2–3% loss in selectivity to cumene hydroperoxide.

The catalyst used to effect this reaction is preferably an acidic clay catalyst or a silica catalyst treated with phosphoric acid.

In the first embodiment the impurities are removed by passing the recycle cumene over a clay catalyst. The clays used as the catalyst to effect this reaction are montmorillonite silica-alumina clays. A variety of clay catalysts containing aluminum and silica are effective, however it is preferable that the alumina or silica be acidic under normal operating conditions. As discussed, a group of catalysts which works well in this synthesis are acidic clay mineral catalysts. Chemically clays are composed primarily of silicon, aluminum and oxygen, with minor amounts of magnesium and iron in some cases. Variations in the ratios of these constituents, and their crystal lattice configurations, result in some fifty separate clays, each with its own characteristic properties.

Particularly effective in the reaction are smectite clays. Smectite clays are discussed in an article cited in Chem. Systems Report, 84-3, "Catalysis: Selective Developments," *Chem. Systems Report* 84-3, 239-249, at Section 3.4320. These clays have small particle size and unusual intercalation properties which afford them high surface area. They are aluminosilicates with a unique structure that permits modifications which provide useful catalysts. They comprise layered sheets of octahedral sites between sheets of tetrahedral sites, and the distance between the layers can be adjusted by swelling, through treatment with the appropriate solvent, or treatment with a pillaring or Lewis acid reagent etc. What renders the smectites of particular interest among the clay minerals is their combination of cation exchange, intercalation and swelling properties.

The three-layered sheet types of smectite clays include montmorillonite, vermiculite and certain micas, all of which may be expanded between their layers by the appropriate treatment. The idealized basic structure of clays of this type is that of a pyrophyllite which has the basic formula $Si_8Al_4O_{20}(OH)_4$.

A general representation of the montmorillonite structure is:

$$M_{x/n}{}^{n+} \cdot yH_2O(Al_{4-x}Mg_x)(Si_8)O_{20}(OH)_4$$

where M represents the interlamellar (balancing cation, normally sodium or lithium and x, y and n are integers.

These montmorillonite clays are best used in the present application in an acidic form. Acids, particularly mineral acids such as sulfuric or phosphoric acids, activate montmorillonites by attacking and solubilizing structural cations in the octahedral layers. This opens up the clay structure and increases surface area. These acid-treated, particularly mineral acid treated, clays act as strong Bronsted acids.

Acid montmorillonite clays are the preferred form of smectite clay in the present invention. Preferably these acid clays should have acidities in the range of 3 to 20, or greater, mg KOH/gm, titrated to a phenolphthalein end point. Their surface area should be $> 30 \, m^2/g$ and preferably 200 to 1000 $m^2/g$. Their moisture content should be limited also, thereby upon heating to 220° F., the weight loss is generally less than 20 wt. %.

Illustrative examples of suitable montmorillonite clays include powdered clays, such as Engelhard's Filtrol Grade 13, 113 and 160, sold by Engelhard, clays in granular form, such as Filtrol Grade 24, having a 20-60 mesh size, and grade 25 (10/20 mesh) sold by Engelhard, as well as extruded clays such as the Filtrol Clay-62, sold in 1/16" and 3/16" diameter extrudates.

It was surprising that these clays are better for removing impurities than, for example, a super acid catalyst. In Table I, example 10, it is demonstrated that a super acid catalyst did not perform as well as a simple clay.

In the second embodiment removal of 2-phenyl-2-propanol and cumene hydroperoxide from the recycle stream is significantly improved by the presence of a silica catalyst which has been treated with phosphoric acid.

The preparation of the phosphoric acid modified silica is accomplished by treating a silica catalyst with phosphoric acid. The phosphoric acid and silica are mixed for 2 minutes to 20 hours at a temperature of about 20° C. to 280° C. The preferred temperature is from 25° C. to 180° C. The time period can be shorter. The mixture is then filtered, the solid washings washed until the washings no longer show detectable levels of H+ ions and the final product dried in vacuo at 140° C. for 3 days.

According to this procedure a solution of 85% $H_3PO_4$(20 g) in water (180 g) was added with slurry to 100 g of silica gel grade 57. The acid was absorbed into the silica with gentle slurry for 5-10 minutes. The mixture was then filtered and dried at 140° C. for 3 days and required 10-30 mesh material was used.

The wt. % of phosphoric acid to the silica support should be such that the concentration of phosphorous is in the range of 0.1 wt. % to 10 wt. %, although concentration outside this range may also be used.

The silica may be in the form of powders, pellets, spheres and extrudates.

The purification of the cumene recycle stream may be conducted batchwise, in a continuous slurry bed reactor, or in a fixed bed, continuous flow, reactor. For practical reasons a fixed bed is preferred. In all cases the catalyst concentration should be sufficient to provide the desired catalytic effect.

Purification of the cumene recycle stream can generally be conducted at temperatures from 0° C.-200° C.; the preferred range is 25° C.-125° C. The operating pressure may be from zero to 1000 psig, or higher. The preferred pressure range is atm to 300 psig.

The purification is accomplished employing a total liquid hourly space velocity (LHSV) of 0.10 to 10 under mild conditions.

Here the LHSV is defined as follows:

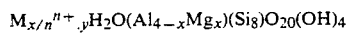

$$LHSV = \frac{\text{Through the Reactor Per Hour}}{\text{Volume of Catalyst in Reactor}}$$

It is understood that the examples given are only for illustration and that the instant invention is not intended to be limited thereby.

The GC analysis of the feed is shown in Example 1. It will be noted that the cumene hydroperoxide is completely destroyed and 2-phenyl-2-propanol has been reduced by a minimum of 94% using the Harshaw Clay-24. Harshaw super acid catalyst did not provide anywhere near as good results. The best results were 96% reduction for CHP and only 79% reduction for 2-phenyl-2-propanol [see Example 10]. Similar good results are obtained with Clay-62 and with Clay-25.

PURIFICATION OF RECYCLE CUMENE[a]

| Ex. | Temp. (°C.) | Reaction[a] (PSIG) | Liq. Rate (CC/HR) | Catalyst | Products, Acetone[c] | Area % Cumene[c] | Phenol[c] | α-Me.Styr. | Acetophenone[c] | 2-Ph-2-PrOH[c] | CHP[c] | Heavies[c] |
|---|---|---|---|---|---|---|---|---|---|---|---|---|
| 1 | — | — | — | Harshaw Clay-24 | 0.066 | 97.045 | 0.036 | 0.195 | 0.130 | 1.121 | 1.312 | 0.009 |
| 2 | 83 | 100 | 100 | " | 0.382 | 93.735 | 0.445 | 0.164 | 0.236 | 0.073 | 0 | 1.191 |
| 3 | 80 | 100 | 100 | " | 0.234 | 96.795 | 0.203 | 0.124 | 0.296 | 0.027 | 0 | 1.359 |
| 4 | 100 | 100 | 100 | " | 0.307 | 97.361 | 0.287 | 0.144 | 0.251 | 0.019 | 0 | 1.305 |
| 5 | 60 | 100 | 100 | " | 0.468 | 97.173 | 0.487 | 0.172 | 0.198 | 0.016 | 0 | 1.235 |
| 6 | 4 | 100 | 100 | " | 0.442 | 97.263 | 0.457 | 0.292 | 0.214 | 0.017 | 0 | 1.114 |
| 7 | 40 | 100 | 100 | " | 0.495 | 97.284 | 0.579 | 0.397 | 0.176 | 0.018 | 0 | 0.882 |
| 8 | 80 | 100 | 100 | " | 0.740 | 96.444 | 0.749 | 0.244 | 0.224 | 0.012 | 0 | 1.394 |
| 9 | 80 | 100 | 100 | Harshaw Super Acid | 0.226 | 95.554 | 0.208 | 0.397 | 0.125 | 0.562 | 0.258 | 0.033 |
| 10 | 80 | 100 | 100 | Harshaw Super Acid | 0.329 | 97.813 | 0.455 | 0.538 | 0.140 | 0.240 | 0.046 | 0.061 |
| 11 | 60 | 100 | 100 | Harshaw Super Acid | 0.272 | 96.542 | 0.442 | 0.261 | 0.158 | 0.607 | 0.756 | 0.053 |
| 12 | 60 | 100 | 100 | Harshaw Super Acid | 0.063 | 97.154 | 0.087 | 0.217 | 0.125 | 0.627 | 1.008 | 0.010 |
| 13 | 40 | 100 | 100 | Harshaw Super Acid | 0 | 97.208 | 0.259 | 0.018 | 0.135 | 0.800 | 1.120 | 0.009 |
| 14 | 40 | 100 | 100 | Harshaw Super Acid | 0.045 | 97.089 | 0.052 | 0.203 | 0.130 | 0.975 | 1.305 | 0.009 |
| 15 | 80 | 100 | 100 | Harshaw Clay-62 | 0.335 | 96.021 | 0.652 | 0.507 | 0.123 | 0.040 | 0.046 | 0.233 |
| 16 | 80 | 100 | 100 | " | 0.436 | 96.731 | 0.768 | 0.484 | 0.136 | 0.013 | 0 | 0.535 |
| 17 | 60 | 100 | 100 | " | 0.506 | 97.182 | 0.765 | 0.448 | 0.148 | 0.020 | 0 | 0.563 |
| 18 | 60 | 100 | 100 | " | 0.497 | 97.422 | 0.721 | 0.425 | 0.141 | 0.038 | 0.005 | 0.490 |
| 19 | 40 | 100 | 100 | " | 0.455 | 97.469 | 0.662 | 0.316 | 0.153 | 0.097 | 0.021 | 0.578 |
| 20 | 40 | 100 | 100 | " | 0.447 | 97.798 | 0.479 | 0.305 | 0.154 | 0.224 | 0.077 | 0.289 |
| 21 | 100 | 100 | 100 | Harshaw Clay-25 | 0.089 | 98.579 | 0.159 | 0.065 | 0.146 | 0 | 0 | 0.818 |
| 22 | 100 | 100 | 100 | " | 0.383 | 98.029 | 0.234 | 0.094 | 0.207 | 0 | 0 | 0.919 |
| 23 | 80 | 100 | 100 | " | 0.474 | 97.664 | 0.520 | 0.174 | 0.194 | 0.006 | 0 | 0.829 |
| 24 | 80 | 100 | 100 | " | 0.457 | 97.793 | 0.455 | 0.163 | 0.183 | 0.005 | 0 | 0.804 |
| 25 | 60 | 100 | 100 | " | 0.446 | 97.684 | 0.511 | 0.363 | 0.196 | 0.011 | 0 | 0.706 |
| 26 | 60 | 100 | 100 | " | 0.595 | 97.393 | 0.724 | 0.436 | 0.186 | 0.016 | 0 | 0.523 |

In Table II the GC analysis of the feed is shown in Example 28. Examples 29 through 32 show that SiO$_2$ alone does not remove cumene hydroperoxide or 2-phenyl-2-propanol. The other experiments show quite clearly that phosphoric acid on silica [SiO$_2$/H$_3$PO$_4$] does remove cumene hydroperoxide and 2-phenyl-2-propanol under a variety of conditions.

PURIFICATION OF RECYCLE CUMENE[a]

| Ex. | Temp. (°C.) | Reaction[a] (PSIG) | Liq. Rate (CC/HR) | Catalyst | Products, Acetone[c] | Area % Cumene[c] | Phenol[c] | α-Me.Styr. | Acetophenone[c] | 2-Ph-2-PrOH[c] | CHP[c] | Heavies[c] |
|---|---|---|---|---|---|---|---|---|---|---|---|---|
| 27 | — | — | — | — | 0.066 | 97.045 | 0.036 | 0.195 | 0.130 | 1.121 | 1.312 | 0.009 |
| 28 | 80 | 100 | 100 | Davidson Silica Gel Grade 57 | 0.055 | 96.798 | 0.022 | 0.192 | 0.141 | 1.181 | 1.496 | 0.010 |
| 29 | 80 | 100 | 100 | Davidson Silica Gel Grade 57 | 0.066 | 96.727 | 0.017 | 0.192 | 0.135 | 1.171 | 1.541 | 0.009 |
| 30 | 60 | 100 | 100 | Davidson Silica Gel Grade 57 | 0.036 | 96.973 | 0 | 0.211 | 0.134 | 0.975 | 1.466 | 0.023 |
| 31 | 60 | 100 | 100 | Davidson Silica Gel Grade 57 | 0.028 | 96.766 | 0 | 0.200 | 0.134 | 1.094 | 1.628 | 0.015 |
| 32 | 80 | 100 | 100 | SiO$_2$/H$_3$PO$_4$[b] | 0.758 | 96.143 | 1.139 | 0.154 | 0.149 | 0.013 | 0.019 | 1.465 |
| 33 | 80–40 | 100 | 100 | " | 0.991 | 96.030 | 1.535 | 0.561 | 0.140 | 0 | 0 | 0.650 |
| 34 | 80 | 100 | 100 | " | 0.758 | 96.758 | 0.814 | 0.183 | 0.132 | 0 | 0 | 1.230 |
| 35 | 60 | 100 | 100 | " | 0.569 | 92.247 | 0.716 | 0.350 | 0.130 | 0 | 0 | 0.893 |
| 36 | 60 | 100 | 100 | " | 0.549 | 97.274 | 0.650 | 0.241 | 0.131 | 0 | 0 | 1.060 |
| 37 | 40 | 100 | 100 | " | 1.293 | 96.566 | 0.737 | 0.496 | 0.129 | 0 | 0 | 0.683 |
| 38 | 40 | 100 | 100 | " | 1.496 | 96.527 | 0.729 | 0.621 | 0.128 | 0 | 0 | 0.446 |
| 39 | 100 | 100 | 100 | " | 0.588 | 96.905 | 0.639 | 0.247 | 0.144 | 0 | 0 | 1.376 |
| 40 | 100 | 100 | 100 | " | 0.646 | 96.750 | 0.778 | 0.272 | 0.142 | 0 | 0 | 1.311 |
| 41 | 120 | 100 | 100 | " | 0.673 | 96.688 | 0.672 | 0.275 | 0.145 | 0 | 0 | 1.429 |
| 42 | 120 | 100 | 100 | " | 0.650 | 96.732 | 0.801 | 0.418 | 0.143 | 0 | 0 | 1.151 |
| 43 | 140 | 100 | 100 | " | 0.590 | 96.726 | 0.875 | 0.907 | 0.146 | 0 | 0 | 0.655 |
| 44 | 140 | 100 | 100 | " | 0.489 | 96.776 | 0.727 | 0.932 | 0.148 | 0.021 | 0 | 0.797 |

[a]The reactor was a 19½" × 0.51" (ID) stainless steel tube. The catalyst bed was 100 cc. Liquid feed was pumped into the bottom of the reactor. Pressure regulation was with a Skinner Uni-Flow valve and a Foxboro controller. The reactor was electrically heated. The liquid feed was pumped with a Ruska dual drive pump. A 300 cc prerun was taken at each temperature and then 200 cc of sample.
[b]100 g Davidson Silica gel grade 57 was mixed with 20 g 85% H3PO4 and 180 g DM H2O. This slurry was then mixed gently for 5–10 minutes and filtered. The solid was dried at 140° C. for 3 days and sieved. 10–30 mesh material was used.
[c]Determined by GC analysis of reactor effluent.

What is claimed is:
1. A method for purifying a cumene recycle stream by removing 2-phenyl-2-propanol and cumene hydro- peroxide before the cumene is distilled and recycled to the peroxidation reactor which comprises reacting the recycle cumene in the presence of an acid treated montmorillonite clay of the formula:

$$M_{x/n}{}^{n+} \cdot yH_2O(Al_{4-x}Mg_x)(Si_8)O_{20}(OH)_4$$

2. The method of claim 1 wherein the clay is treated with a mineral acid.

3. The method of claim 2 wherein the mineral acid is selected from the group consisting of sulfuric acid and phosphoric acid.

4. The method of claim 1 wherein the purification is accomplished at a temperature of from 25° C. to 180° C.

5. A method for removing impurities, including 2-phenyl-2-propanol and cumene hydroperoxide, from a cumene recycle stream before the cumene is distilled and recycled to the peroxidation reactor which comprises reacting the cumene in the presence of a catalyst comprising a phosphoric acid supported on silica.

6. The method of claim 4 wherein the purification is accomplished at a temperature between about 25° C. and 125° C.

* * * * *